(12) United States Patent
Braun (10) Patent No.: US 7,302,726 B2
(45) Date of Patent: Dec. 4, 2007

(54) TOOTHBRUSHES

(75) Inventor: Phillip M. Braun, Exeter, RI (US)

(73) Assignee: Braun GmbH (DE)

( * ) Notice: Subject to any disclaimer, the term of this patent is extended or adjusted under 35 U.S.C. 154(b) by 697 days.

(21) Appl. No.: 10/445,103

(22) Filed: May 23, 2003

(65) Prior Publication Data

US 2004/0231078 A1    Nov. 25, 2004

(51) Int. Cl.
*A61C 17/22* (2006.01)
(52) U.S. Cl. .................. 15/23; 15/28; 15/29
(58) Field of Classification Search ............. None
See application file for complete search history.

(56) References Cited

U.S. PATENT DOCUMENTS

| | | | |
|---|---|---|---|
| 864,201 A | 8/1907 | Shers | |
| 1,577,751 A | 3/1926 | Paschall | |
| 1,981,688 A | 11/1934 | Conti | 15/28 |
| 1,997,352 A | 4/1935 | Fleet | 15/22.1 |
| 2,140,307 A | 12/1938 | Belaschk et al. | |
| 3,524,088 A | 8/1970 | Ryckman | |
| 3,538,530 A | 11/1970 | Stemme | |
| 3,546,501 A | 12/1970 | Kircher | |
| 4,027,348 A | 6/1977 | Flowers et al. | |
| 4,102,084 A | 7/1978 | Bloomquist | |
| 4,175,299 A | 11/1979 | Teague, Jr. et al. | |
| 4,177,535 A | 12/1979 | Cole | |
| 4,276,672 A | 7/1981 | Teague, Jr. et al. | |
| 4,336,622 A | 6/1982 | Teague, Jr. et al. | |
| 4,571,768 A | 2/1986 | Kawashima | |
| 4,791,945 A | 12/1988 | Moriyama | |
| 4,802,255 A | 2/1989 | Breuer et al. | |
| 4,854,085 A | 8/1989 | Huber | |
| 5,504,959 A | 4/1996 | Yukawa et al. | |
| 5,577,285 A | 11/1996 | Drossler | |
| 5,651,157 A | 7/1997 | Hahn | |
| 5,652,990 A | 8/1997 | Driesen et al. | |
| 5,687,442 A | 11/1997 | McLain | |
| 5,784,743 A | 7/1998 | Shek | |
| 5,862,558 A | 1/1999 | Hilfinger et al. | 15/28 |
| 6,446,295 B1 | 9/2002 | Calabrese | |
| 6,679,768 B2 | 1/2004 | Nemoto | |
| 2002/0066147 A1 | 6/2002 | Schutz | |
| 2003/0031979 A1 | 2/2003 | Shortt et al. | 433/118 |
| 2003/0084524 A1 | 5/2003 | Blaustein et al. | |
| 2003/0084526 A1 | 5/2003 | Brown et al. | |
| 2003/0084527 A1 | 5/2003 | Brown et al. | |
| 2003/0126700 A1* | 7/2003 | Jeng et al. | 15/28 |
| 2003/0163882 A1 | 9/2003 | Blaustein et al. | |

(Continued)

FOREIGN PATENT DOCUMENTS

DE    4243220    6/1994

(Continued)

OTHER PUBLICATIONS

Web page document www.solidsurfacemagazine.com "Random Orbit Sanders" Solid Surface new p. 65.

*Primary Examiner*—David Redding
(74) *Attorney, Agent, or Firm*—Fish & Richardson P.C.

(57) ABSTRACT

Power toothbrushes are provided having toothbrush heads that move in a substantially random manner when in use and in contact with a user's teeth.

16 Claims, 6 Drawing Sheets

U.S. PATENT DOCUMENTS

| | | |
|---|---|---|
| 2004/0128780 A1 | 7/2004 | Chan |
| 2004/0177458 A1 | 9/2004 | Chan et al. |
| 2005/0188483 A1* | 9/2005 | Scherl ................... 15/22.1 |

FOREIGN PATENT DOCUMENTS

| | | |
|---|---|---|
| DE | 4318976 | 12/1994 |
| EP | 0765642 B1 | 2/2002 |
| GB | 2371217 A | 7/2002 |
| WO | WO98/14092 | 4/1998 |
| WO | WO03/011162 | 2/2003 |
| WO | WO2004/041114 A1 | 5/2004 |

* cited by examiner

TOOTHBRUSHES

TECHNICAL FIELD

This invention relates to toothbrushes, and more particularly to power toothbrushes.

BACKGROUND

Power toothbrushes are well known and have been on the market for years. In typical power toothbrushes, tufts of bristles on the brush head extend generally perpendicularly from the top surface of the head. The head is oscillated, rotated and/or translated in order to provide enhanced tooth cleaning capability. Generally, the head moves in a substantially fixed path over the surface of the user's teeth.

SUMMARY

In one aspect, the invention features a power toothbrush including a handle, a toothbrush head that extends from the handle and carries a plurality of cleaning elements, and a drive mechanism constructed to cause motion of the toothbrush head. The toothbrush head is configured to move in a substantially random path when the drive mechanism is actuated and the cleaning elements are brought into contact with a user's teeth.

In some embodiments, the drive mechanism drives the toothbrush head in an orbital motion about an axis that is spaced from the axis of the toothbrush head.

In some cases, the drive mechanism includes a bevel gear. The toothbrush head can be mounted on the bevel gear. The toothbrush head can be mounted on a shaft that extends through a bore in the bevel gear, the shaft being mounted to spin freely within the bore. In some embodiments, the shaft is disposed at an angle (e.g., from about 2° to about 7°) with respect to a center axis of the bevel gear. In some cases, the bore is offset from a center axis of the bevel gear. The bore can be offset from the center axis by about 1 mm to about 3 mm. The bevel gear can include an O-ring disposed between a lower surface of the toothbrush head and an upper surface of the bevel gear. The upper surface of the bevel gear can include a counterbore that is configured so that the O-ring rests on a plane that is perpendicular to a center axis of the bore. In some cases, there is sufficient clearance between the bore and the shaft to allow the shaft to move radially within the bore.

In some embodiments, the toothbrush is configured so that when the toothbrush is in use, the motion of the toothbrush head is determined by a fluctuating sticking and slipping of a surface of the toothbrush head on a surface of the drive mechanism.

In some cases, the cleaning elements include bristles. In some embodiments, the cleaning elements include bristle tufts.

In another aspect, the invention features a method of brushing the teeth of a mammal. The method includes providing a power toothbrush that has a handle, a toothbrush head extending from the handle and carrying a plurality of cleaning elements, and a drive mechanism that causes the toothbrush head to move. The toothbrush is configured so that the toothbrush head will move in a substantially random path when the drive mechanism is actuated and the cleaning elements are brought into contact with a user's teeth. The method further includes contacting the teeth with the cleaning elements while the drive mechanism is actuated.

In another aspect, the invention features a power toothbrush including a handle, a toothbrush head extending from the handle and carrying a plurality of cleaning elements, and a drive mechanism. The drive mechanism is constructed to drive the toothbrush head in an orbital motion about an axis spaced from the axis of the toothbrush head. The drive mechanism includes a bevel gear. The toothbrush head is mounted on a shaft that extends through a bore defined by the bevel gear. The shaft is mounted to spin freely within the bore.

In some embodiments, the shaft is disposed at an angle with respect to a center axis of the bevel gear. In some cases, the bore is offset from a center axis of the bevel gear.

In another aspect, the invention features a power toothbrush including a handle, a toothbrush head extending from the handle and carrying a plurality of cleaning elements, and a drive mechanism that is constructed to cause the toothbrush head to move. The drive mechanism drives the toothbrush head in an orbital motion.

In some embodiments, the orbital motion is about an axis spaced from the axis of the toothbrush head. The drive mechanism can include a bevel gear.

In some cases, the toothbrush head is configured to move in a substantially random path when the drive mechanism is actuated and the cleaning elements are brought into contact with a user's teeth.

Other features and advantages of the invention will be apparent from the description and drawings, and from the claims.

DETAILED DESCRIPTION

Figure 1:
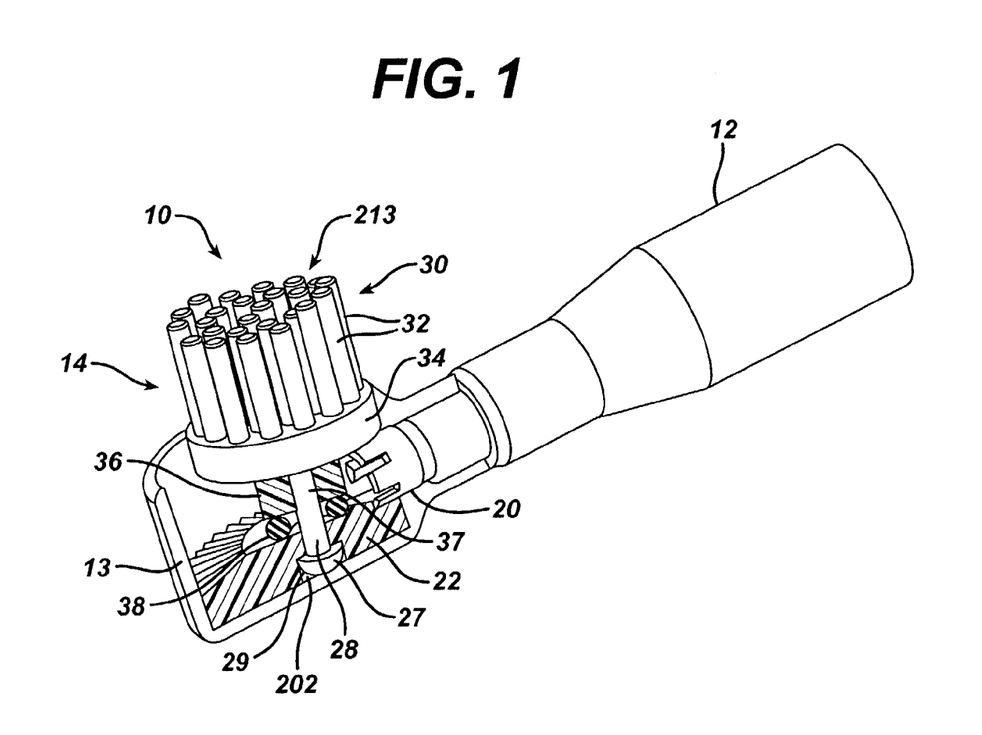
FIG. 1 is a perspective view in partial cross-section, with a portion of the housing removed, of an embodiment of a power toothbrush.

Referring to FIG. 1, a power toothbrush 10 includes a housing 12, and a brushing portion 14 extending from the housing. The brushing portion 14 includes a shroud 13 and a toothbrush head 30 mounted within the shroud 13. A drive shaft (not shown) is disposed within the housing, and is driven by a driving mechanism (e.g., an electric motor) to turn a gear 20. Gear 20 in turn drives a bevel gear 22 which causes the toothbrush head 30 to orbitally rotate, as will be discussed below. Bevel gear 22 typically rotates at a velocity of about 750-2000 rotations per minute (RPM).

The toothbrush head 30 includes a spinning shaft 28. One end of spinning shaft 28 is mounted to spin freely within a bore 202 in bevel gear 22, and includes a cap 27 of greater diameter than the bore 202 to retain the spinning shaft 28 in the bore. Cap 27 is seated in a recess 29.

The toothbrush head 30 includes a plurality of bristle tufts 32 mounted on a support member 34, which is fixedly mounted on the other end of spinning shaft 28. Although each tuft is shown as a solid mass in the drawings, the tufts are actually each made up of a great mass of individual plastic bristles. The bristles may be made of any desired polymer, e.g., nylon 6.12 or 6.10, and may have any desired diameter, e.g., 4-8 mil. The tufts are supported at their bases by the support member 34, and may be held in place by any desired tufting technique as is well known in the art, e.g., hot tufting or a stapling process. The tufts have a length of between about 4 mm and about 12 mm, and preferably have a length of about 8 mm.

The support member 34 includes a lower portion 36. The lower portion 36 has a diameter of between about 6 mm and about 18 mm, and preferably has a diameter of about 14 mm. One end of spinning shaft 28 is disposed within a bore 37 in lower portion 36.

Figure 2:
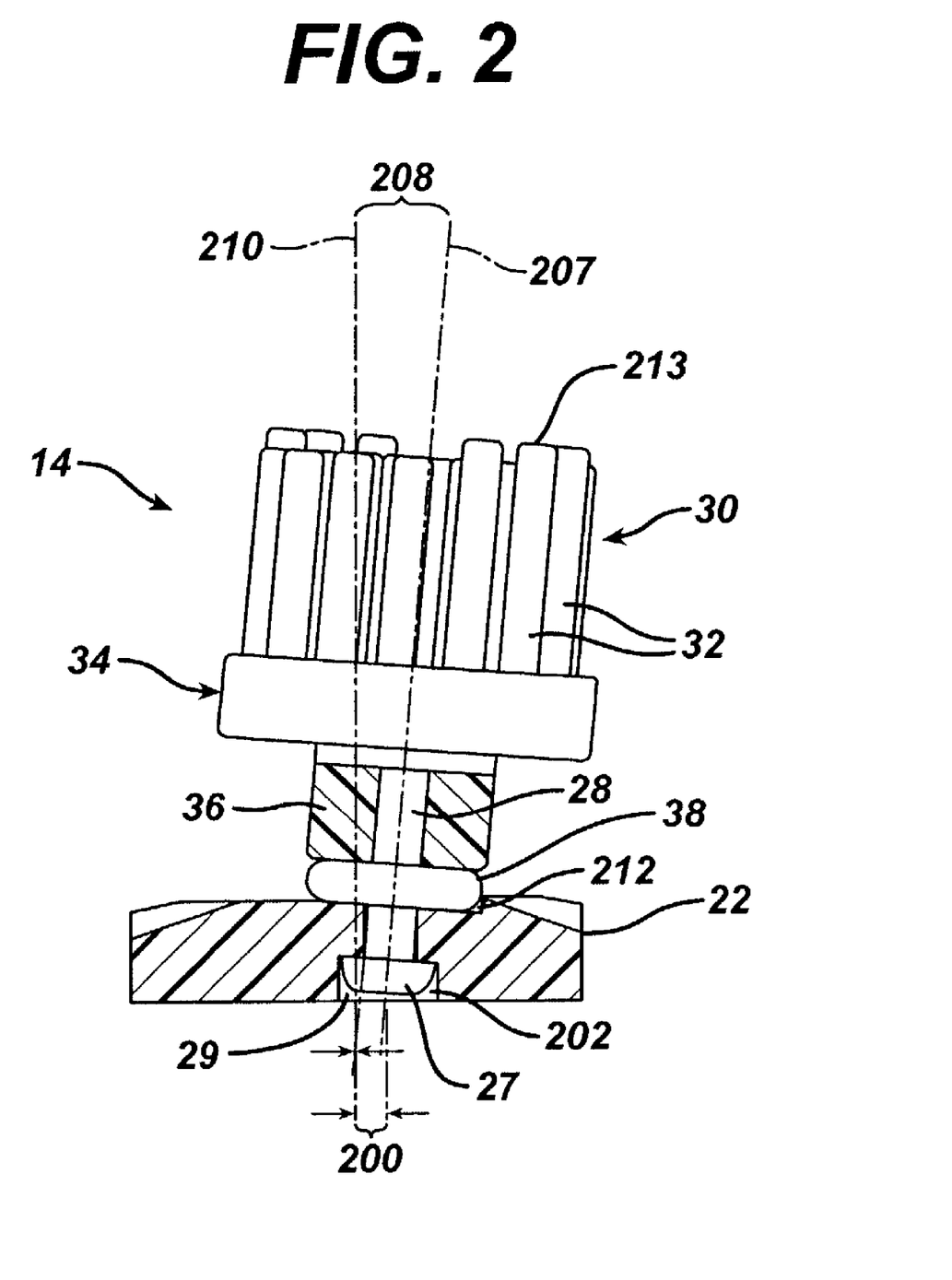
FIG. 2 is a side view in partial cross-section of an embodiment of a brush head of the power toothbrush shown in FIG. 1.

Referring also to FIG. 2, the brushing portion 14 further includes a resilient O-ring 38, disposed between lower portion 36 and bevel gear 22. The O-ring has a diameter that is approximately the same as that of lower portion 36, for reasons that will be discussed below. Spinning shaft 28 is tilted at an angle 208 (e.g., five degrees) relative to a gear axis of rotation 210. Because spinning shaft 28 is tilted at an angle, toothbrush head 30 is also tilted at an angle. The bevel gear 22 includes a counterbore 212. The counterbore 212 is designed to cause O-ring 38 to be seated with its center axis disposed at the same angle as the center axes 207 of bore 202 and spinning shaft 28.

Spinning shaft 28 is also located at an offset distance 200 relative to the center of bevel gear 22. When toothbrush 10 is in operation, spinning shaft 28 and, therefore, toothbrush head 30 (which is mounted on spinning shaft 28), orbits about the axis of rotation 210 of bevel gear 22. When a load is applied to the toothbrush head 30, e.g., when the bristles contact a user's teeth, toothbrush head 30 will spin about axis 207 of spinning shaft 28, as will be discussed below. As a result, when it is in use and under load, toothbrush head 30 moves in a path that includes both orbital and spinning motion.

Spinning shaft 28 extends through and spins freely within bore 202 in bevel gear 22. The spinning shaft 28 does not fit tightly within bore 202; instead, there is clearance between spinning shaft 28 and the wall of bore 202. Moreover, the cap 27 of shaft 28 can move freely within recess 29. Because of the clearance between spinning shaft 28 and bore 202, the shaft can move axially in response to pressure exerted on the upper surface 213 of tufts 32, displacing cap 27 axially. These clearances also allow the toothbrush head 30 to pivot about the bore 202.

Figure 2A:
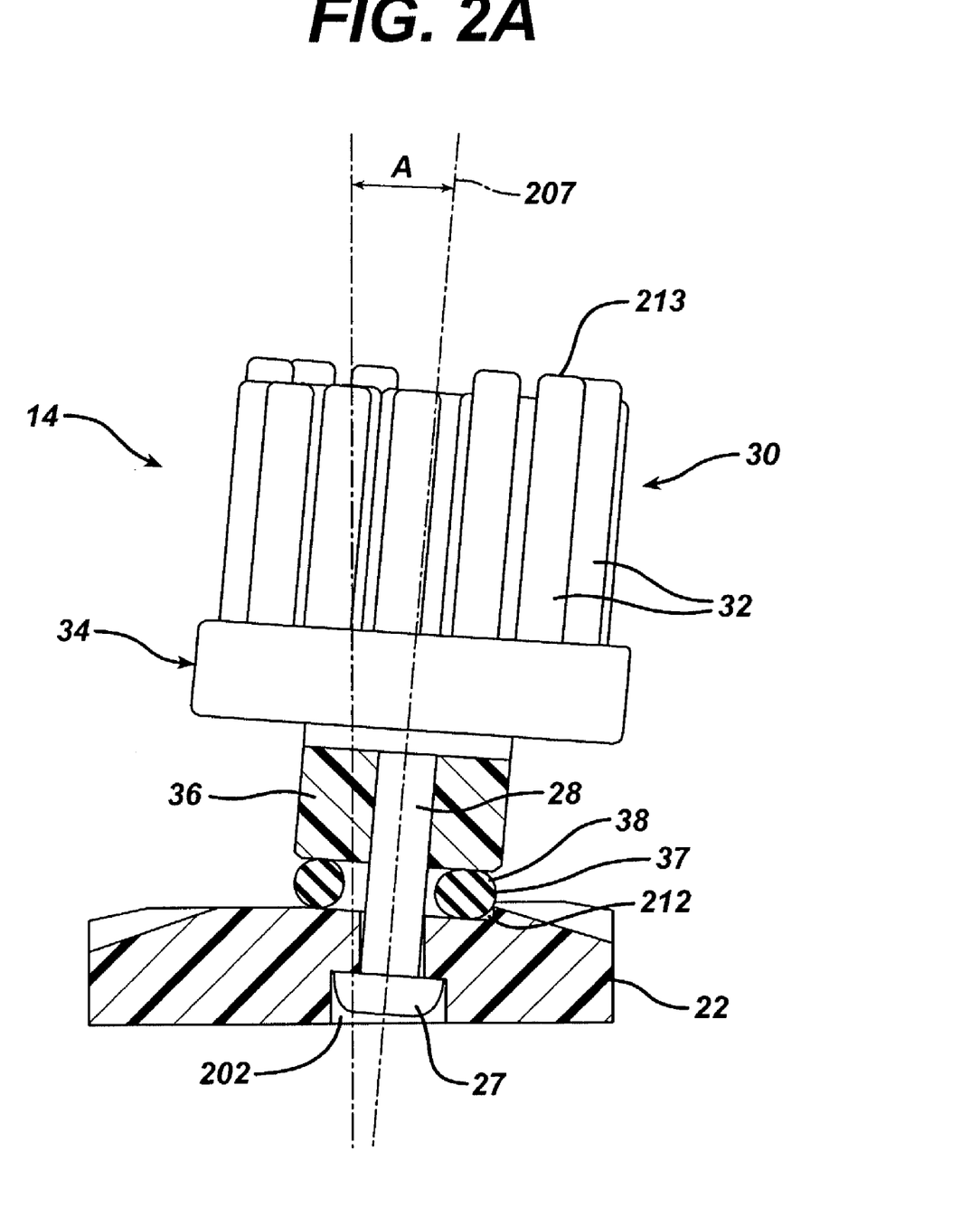
FIG. 2A is similar to FIG. 2, but shows the brush head in operation without a load (i.e., not contacting the teeth).

When the brush is activated, centripetal force throws toothbrush head 30 outward to the greatest angle allowed by the clearances discussed above, i.e., an angle greater than angle 208, typically about 7 degrees (angle A, FIG. 2A). In this position, the outer portion 37 of O-ring 38 is compressed by lower portion 36 of support member 34. This compression results in friction which, in turn, effectively causes engagement of lower portion 36 with the surface of counterbore 212.

Figure 3:
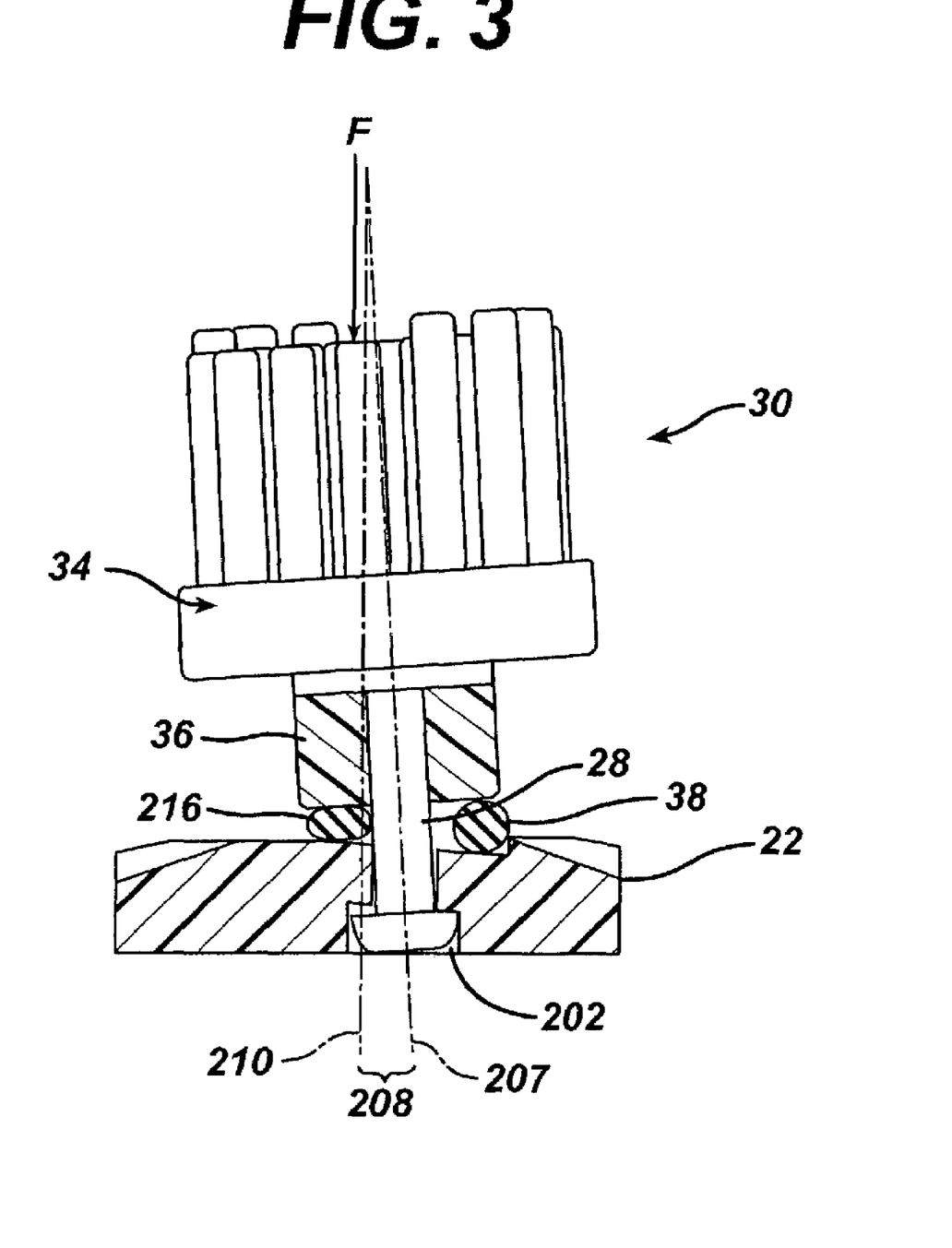
FIG. 3 is similar to FIG. 2, but shows the brush head in operation with a load applied (i.e., contacting the teeth).

Referring now to FIG. 3, when a toothbrush user places toothbrush 10 against her teeth, a force F is applied to toothbrush head 30. Referring to FIG. 2A, because it is tilted, toothbrush head 30 initially contacts the teeth at an angle. When a force F that is greater than the centripetal force is applied to toothbrush head 30, toothbrush head 30 tries to right itself in response, and axis 207 of shaft 28 begins to move toward axis of rotation 210, decreasing angle A. This movement of the shaft 28 disrupts the effective engagement between lower portion 36 and bevel gear 22. The shaft 28 moves toward the axis of rotation 210 until shaft 28 is bound in bore 202, and toothbrush head 30 is in the position shown in FIG. 3. In this position, the inner region 216 of O-ring 38 is compressed; i.e., the inner region 216 of the O-ring 38 is pinched between counterbore 212 and lower portion 36.

Figure 4:
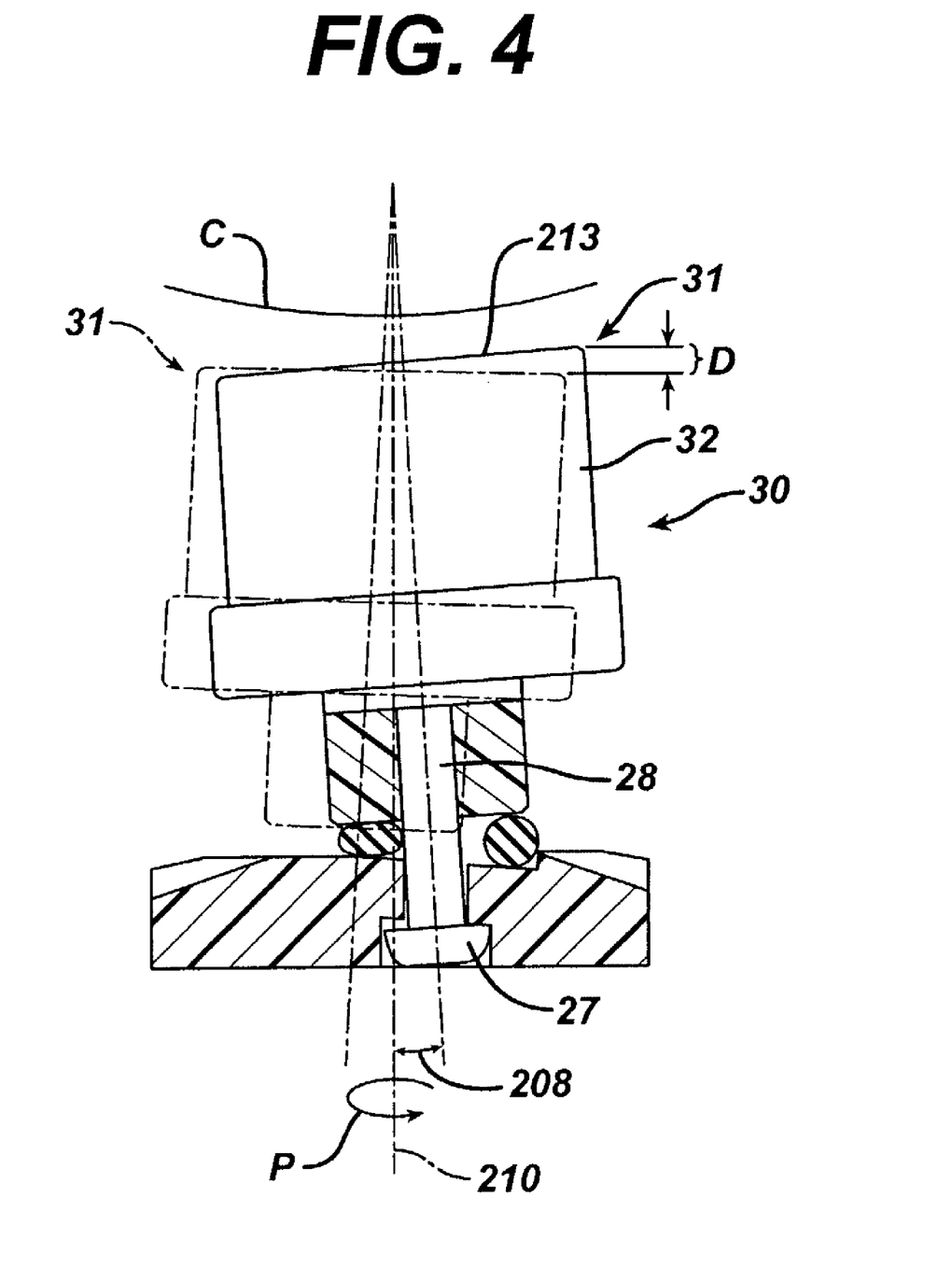
FIG. 4 is similar to FIG. 3, but shows movement of the brush head (indicated by phantom lines).
Figure 4A:
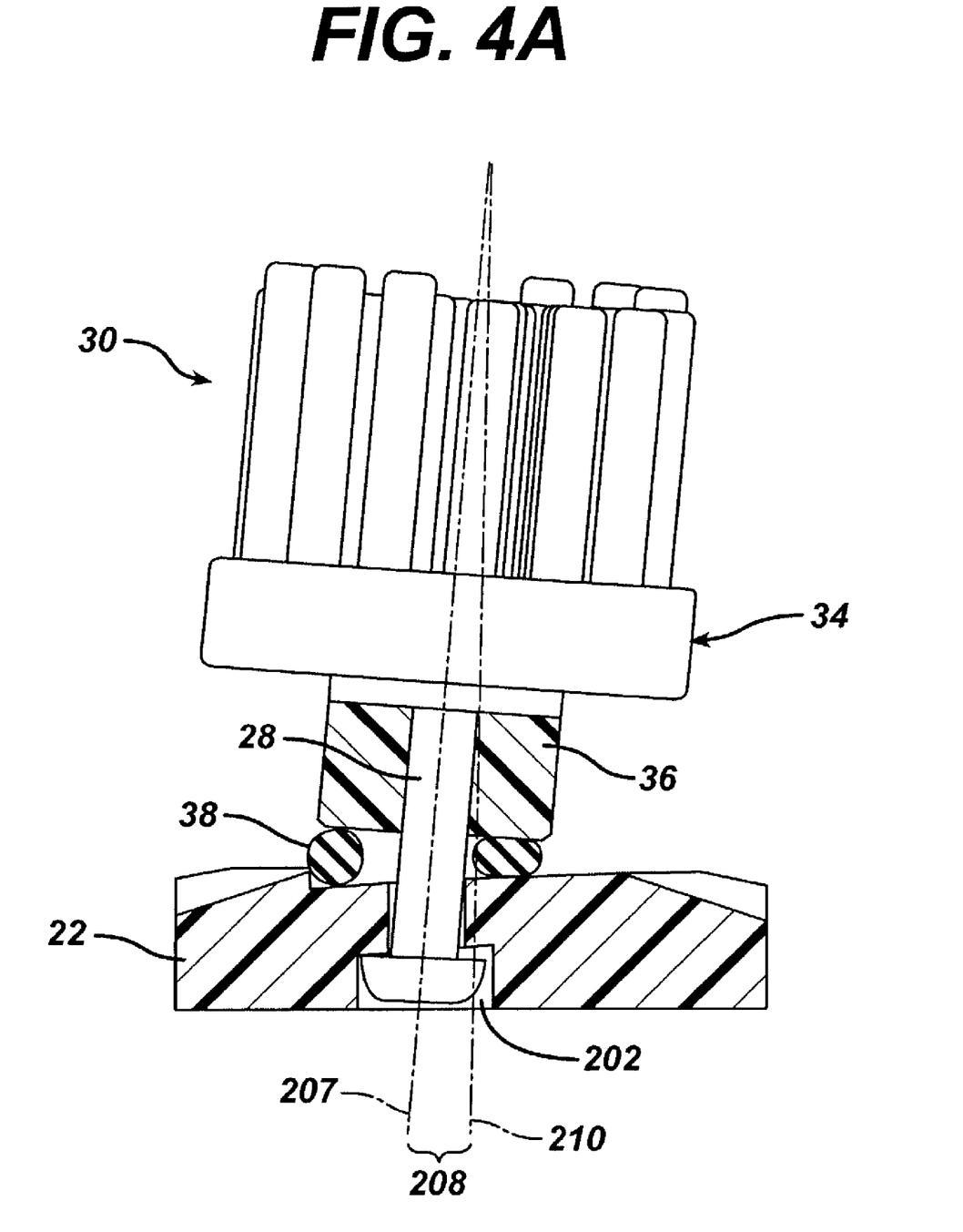
FIG. 4A is similar to FIG. 4, but shows the position of the brush head when the bevel gear has rotated 180° relative to its position in FIG. 3 (shown in solid lines in FIG. 4).

The general motion of toothbrush head 30, when it is contacting the teeth, is shown schematically in FIG. 4. The phantom lines in FIG. 4 show the position of the head when the bevel gear has rotated 180 degrees, which is a mirror image about axis 210 of the initial position of the head, indicated by the solid lines in FIG. 4. The position of the entire brushing portion when the bevel gear has rotated 180 degrees from the position shown in FIG. 3 is shown in solid lines in FIG. 4A. Referring back to FIG. 4, because the toothbrush head 30 is tilted at an angle, as the toothbrush head 30 spins it rocks back and forth, so that the upper surface 213 of tufts 32 traces a cup-shaped pattern, indicated schematically by line C. Additionally, because the toothbrush head 30 rocks back and forth, the tufts 32 around the perimeter 31 of the toothbrush head move up and down over a distance D.

As long as no load is applied to toothbrush head 30, the toothbrush head will orbit about axis 210 of bevel gear 22 at a constant velocity equal to that of bevel gear 22. When an axial force is applied, toothbrush head 30 also begins to spin about its own axis 207. Tilting of the toothbrush head toward the gear axis 210, with constantly changing forces and binding of the O-ring, creates the effect of an eccentric weight, so that the head spins under load in a random motion. By "random", we mean that during use of the toothbrush, toothbrush head 30 moves in a path that changes as a result of the changing force applied to the bristle tufts 32 when the tufts contact a user's teeth. Generally, the path changes constantly during brushing. This random motion allows the toothbrush user to more easily cover the surface of his teeth and the spaces in between his teeth, without having to intentionally exert an extra effort to achieve such coverage. A factor in the changing direction of the applied force is that the toothbrush 10 is not stationary in the user's hand.

The position of the force applied to the toothbrush head continuously changes during brushing, thus causing the binding and frictional forces to fluctuate. This fluctuation in turn causes a "stick and slip" contact between bevel gear 22 and lower portion 36 of support member 34, transmitted by the O-ring 38. This sticking and slipping occurs in a random, fluctuating manner, resulting in random motion of the toothbrush head 30.

Referring back to FIG. 2, the randomness is increased by the offset distance 200 and the clearances discussed above, which cause spinning shaft 28 to exhibit a jiggling or wobbling motion when toothbrush 10 is in operation. If offset distance 200 were increased, the wobbliness of spinning shaft 28 would become more pronounced, since an increase in circumference of the orbit of rotation of toothbrush head 30 would lead to a corresponding increase in the velocity of toothbrush head 30.

Other embodiments are possible within the scope of the invention.

In some cases, different bristle tufts 32 have a height differential. For example, the tufts around the perimeter of the toothbrush head may be shorter than the tufts at the center of the toothbrush head.

In some embodiments, the power toothbrush 10 does not have an O-ring. The O-ring could be replaced with a rubber flat washer or the bottom of 36 and/or top of 22 could be made of a material that has a rough surface or made of a molded elastomer.

Further embodiments are within the scope of the following claims.

What is claimed is:

1. A power toothbrush comprising:
    a handle;
    a toothbrush head extending from the handle and carrying a plurality of cleaning elements; and
    a drive mechanism constructed to cause motion of the toothbrush head the drive mechanism comprising a bevel gear defining a bore, and a shaft on which the toothbrush head is mounted, the shaft being mounted to extend through and spin freely within the bore and being disposed at an angle with regard to a center axis of the bevel gear,
    wherein the toothbrush head is configured to move in a substantially random path when the drive mechanism is actuated and the cleaning elements are brought into contact with a use's teeth.

2. The toothbrush of claim 1 wherein the drive mechanism drives the toothbrush head in an orbital motion about an axis spaced from the axis of the toothbrush head.

3. The toothbrush of claim 1 wherein the angle is from about 2 to about 7 degrees.

4. The toothbrush of claim 1 wherein the bore is offset from a center axis of the bevel gear.

5. The toothbrush of claim 4 wherein the bore is offset from the center axis by about 1 mm to about 3 mm.

6. The toothbrush of claim 1 wherein the bevel gear includes an O-ring disposed between a lower surface of the toothbrush head and an upper surface of the bevel gear.

7. The toothbrush of claim 6 wherein the upper surface of the bevel gear includes a counterbore configured so that the O-ring rests on a plane that is perpendicular to a center axis of the bore.

8. The toothbrush of claim 1 wherein there is sufficient clearance between the bore and the shaft to allow the shaft to move radially within the bore.

9. The toothbrush of claim 1 wherein the toothbrush is configured so that the motion of the toothbrush head when the toothbrush is in use is determined by a fluctuating sticking and slipping of a surface of the toothbrush head on a surface of the drive mechanism.

10. The toothbrush of claim 1 wherein the cleaning elements comprise bristles.

11. The toothbrush of claim 1 wherein the cleaning elements comprise bristle tufts.

12. A method of brushing the teeth of a mammal, comprising:
    providing a power toothbrush including a handle, a toothbrush head extending from the handle and carrying a plurality of cleaning elements, and a drive mechanism constructed to cause motion of the toothbrush head, the drive mechanism comprising a bevel gear defining a bore, and a shaft on which the toothbrush head is mounted, the shaft being mounted to extend through and spin freely within the bore and being disposed at an angel with regard to a center axis of the bevel gear, the toothbrush being configured so that the toothbrush head will move in a substantially random path when the drive mechanism is actuated and the cleaning elements are brought into contact with a user's teeth; and
    contacting the teeth with the cleaning elements while the drive mechanism is actuated.

13. A power toothbrush comprising:
    a handle;
    a toothbrush head extending from the handle and carrying a plurality or cleaning elements; and
    a drive mechanism constructed to drive the toothbrush head in an orbital motion about an axis spaced from the axis of the toothbrush head, the drive mechanism comprising a bevel gear,
    wherein the toothbrush head is mounted on a shaft that extends through a bore defined by the bevel gear and the shaft is mounted to spin freely within the bore is disposed at an angle with regard to a center axis of the bevel gear.

14. The toothbrush of claim 13 wherein the bore is offset from a center axis of the bevel gear.

15. A power toothbrush comprising:
    a handle;
    a toothbrush head extending from the handle and carrying a plurality of cleaning elements; and
    a drive mechanism constructed to cause motion of the toothbrush head the drive mechanism comprising a bevel gear defining a bore and including an O-ring disposed between a lower surface of the toothbrush head and an upper surface of the bevel gear, and a shaft on which the toothbrush head is mounted, the shaft being mounted to extend through and spin freely within the bore,
    wherein the toothbrush head is configured to move in a substantially random path when the drive mechanism is actuated and the cleaning elements are brought into contact with a user's teeth.

16. A power toothbrush comprising:
    a handle;
    a toothbrush head extending from the handle and carrying a plurality of cleaning elements; and
    a drive mechanism constructed to cause motion of the toothbrush head the drive mechanism comprising a bevel gear defining a bore, and a shaft on which the toothbrush head is mounted, the shaft being mounted to extend through and spin freely within the bore, wherein there is sufficient clearance between the bore and shaft to allow the shaft to move radially within the bore,
    wherein the toothbrush head is configured to move in a substantially random path when the drive mechanism is actuated and the cleaning elements are brought into contact with a user's teeth.

* * * * *